United States Patent
Gasperino et al.

(10) Patent No.: US 10,024,805 B2
(45) Date of Patent: Jul. 17, 2018

(54) METHOD AND DEVICE FOR IDENTIFYING INORGANIC PARTICLES WHICH CONTAMINATE LOADS CONTAINING ORGANIC PARTICLES

(71) Applicant: Rumo Logística Operadora Multimodal S.A., Rio de Janeiro (BR)

(72) Inventors: Vivian de Souza Gasperino, Santos (BR); Ralf Sieves, Santos (BR)

(73) Assignee: Rumo Logística Operadora Multimodal S.A., Rio de Janeiro (BR)

( * ) Notice: Subject to any disclaimer, the term of this patent is extended or adjusted under 35 U.S.C. 154(b) by 193 days.

(21) Appl. No.: 15/104,199

(22) PCT Filed: Dec. 17, 2014

(86) PCT No.: PCT/BR2014/000443
§ 371 (c)(1),
(2) Date: Dec. 20, 2016

(87) PCT Pub. No.: WO2015/089603
PCT Pub. Date: Jun. 25, 2015

(65) Prior Publication Data
US 2017/0089843 A1    Mar. 30, 2017

(30) Foreign Application Priority Data
Dec. 18, 2013    (BR) ..................... 0326062

(51) Int. Cl.
*G01N 21/85*    (2006.01)
*G06T 7/00*    (2017.01)
(Continued)

(52) U.S. Cl.
CPC ......... *G01N 21/94* (2013.01); *G01N 21/6489* (2013.01); *G01N 21/85* (2013.01);
(Continued)

(58) Field of Classification Search
CPC .................... G01N 2021/8592; G06T 7/0004
See application file for complete search history.

(56) References Cited

U.S. PATENT DOCUMENTS 5,410,154 A     4/1995  Broicher et al.
2003/0213299 A1*  11/2003  Arndt ..................... G01F 23/22
                                                        73/290 V
(Continued)

FOREIGN PATENT DOCUMENTS

DE    102012007862 A1    10/2013
JP       2006181603 A  *  7/2006

OTHER PUBLICATIONS

Abdelgawad et al. ("Data fusion framework for sand detection in pipelines," IEEE International Symposium on Circuits and Systems, May 24-27, 2009) (Year: 2009).*
(Continued)

*Primary Examiner* — Yubin Hung
(74) *Attorney, Agent, or Firm* — Patterson + Sheridan, LLP (57) ABSTRACT

The present invention describes a method for identifying inorganic particles which contaminate loads containing organic particles, characterized by including the steps of collecting a sample of the load of organic particles, magnetizing the sample, illuminating the sample, capturing images of the sample and sending the images to a computer for processing, analyzing, and evaluating the images, and finally diagnosing whether the load is contaminated, retaining or releasing the load. The device for identifying inorganic particles which contaminate loads containing organic particles, characterized in that it comprises at least one magnetic field source, at least one lighting source, at least one photographic camera, and a computer.

15 Claims, 7 Drawing Sheets

(51) Int. Cl.
*G01N 21/94* (2006.01)
*G01N 21/95* (2006.01)
*G01N 21/64* (2006.01)
*G01N 21/88* (2006.01)

(52) U.S. Cl.
CPC .............. *G01N 21/88* (2013.01); *G01N 21/95* (2013.01); *G06T 7/0004* (2013.01); *G01N 2021/8592* (2013.01)

(56) References Cited

U.S. PATENT DOCUMENTS

2013/0116339 A1* 5/2013 Gutierrez ........... B01D 19/0036
514/770
2013/0257461 A1* 10/2013 Heidnnann ........ G01R 31/2656
324/703

OTHER PUBLICATIONS

Xiang et al. ("A Reliable and Cost-Effective Sand Monitoring System on the Field Programmable Gate Array (FPGA)," IEEE Transactions on Instrumentation and Measurement, vol. 62, Issue: 7, Jul. 2013) (Year: 2013).*

Sharma et al. ("A combined remote Raman and fluorescence spectrometer system for detecting inorganic and biological materials," Proc. SPIE. 6409, Lidar Remote Sensing for Environmental Monitoring VII, Dec. 12, 2006) (Year: 2006).*

International Search Report, PCT/BR2014/000443, dated Jun. 25, 2015.

* cited by examiner

FIGURA 1

FIGURA 2

FIG. 3

FIGURA 4

METHOD AND DEVICE FOR IDENTIFYING INORGANIC PARTICLES WHICH CONTAMINATE LOADS CONTAINING ORGANIC PARTICLES

The present invention applies to any area where large loads of particulate organic material are transported and/or exported/imported and there is a need to verify whether such loads are contaminated with particulate inorganic material that is not detected by the human eye or not.

PRIOR ART

One will describe hereinafter the present-day procedure of unloading a load of grains or particles of organic material like sugar, for loading it on ships, planes or freight trains.

On grain hoppers, while a truck is being unloaded, a sample of the truck load is taken, to verify the existence or non-existence of impurities or contaminations. Then, one faces the first technical problem: the sample may not represent the reality of the whole load, since this depends on how the sample is taken and by whom it is taken (people are subject to error and corruption).

Currently, exporting/importing companies have contract with inspecting companies to render this service. Further, there is no effective tool that manages to take a sample throughout the whole cross-section of the truck (bucket), as there is for grains.

The sample collected from the truck bucket is placed in a plastic sack identified with the name of the origin of the load (company that produced the load or where it was stored and is sending the product). Then, one faces the second technical problem: since samples from a number of trucks are mixed in the same sack, it is not possible to identify the truck that has unloaded the contaminated load.

With every 1,000 ton unloaded for a given company, such as a plant (each truck unloads 30 ton, on average), the sack of sample of that plant is sealed for laboratory analysis, where, among other factors, one analyzes the amount of insoluble inorganic particles present. The allowed limit of insoluble inorganic particles (any insoluble material, such as sand) is 500 ppm (parts per million), and there may be some variation, depending on the import/export contact. Then, one faces the third problem: if the sample from a given truck was out of specification, but ended up being diluted at levels lower than 500 ppm, since it is placed together with samples from other trucks without contamination, the contamination will not be identified.

The result of a traditional laboratory analysis takes 1 hour, on average. Then, one faces the fourth problem: when some contamination is identified, the load is already within the storehouse, and the contamination often ends up being identified only upon embarkation. At the moment of embarkation, an analysis of insoluble inorganic particles, color and moisture of the particle, such as sugar, is made, but there are cases where the contamination is identified only when the load reaches the client abroad.

This is the worst case, since this may bring consequences even for foreign trade relations, with possible reprisals at the World Trade Organization (WTO).

In addition to this traditional process of the art, on each truck one collects a small sample for carrying out a rapid test for insoluble inorganic particles, by in loco dilution in water and viewing of some portion of water-insoluble residue. This is called "teste do copinho" (little beaker test). Then, one faces the fifth problem: the sample is not representative, the method is imprecise and the process is not reliable (it depends on people and there are no records of it being carried out).

In the face of the above-mentioned problems, the challenges to be overcome by the present invention are:

Identifying contamination in the load of particulate organic material such as a load of sugar received by the importing/exporting company with high affirmativeness, so that;

the whole load of the truck is analyzed individual and instantaneously without human contact (before the load is put in the ware house);

any contamination above 500 ppm is identified in any part of the load; and the contaminated truck is identified, as well as the truck-driver who has transported this load may be prosecuted.

SUMMARY OF THE INVENTION

In order to solve the technical problems and overcome the challenges mentioned above, the present invention is based on the following concept. Although organic particles like sugar, and contaminating inorganic particles like sand, have a number of very similar physicochemical characteristics, there is a significant different between the two of them: conductivity.

Organic particles such as sugar (sucrose), are insulating in nature in the solid state, whereas inorganic particles like sand (silica) have semiconducting characteristics.

It is known that the optical absorption of a semiconducting material is altered by applying a magnetic field, since the electrons are excited from the valence band (less energy) to the conduction band (more energy).

Thus, one has observed that, in spite of none of the two substances exhibiting photoluminescence* characteristics in the normal state, upon application of ultraviolet light (UV), when the inorganic particles like sand (silica) are subjected to a specific field, they begin to exhibit such a property.

\* Photoluminescence is the ability of a substance to emit light when subjected to high energy radiations such as ultraviolet (UV), cathode ray, X-ray and others.

Photoluminescence takes place because the electron decays from the conduction band to the valence band when it is excited by UV. In this process, the electrons are initially promoted to more high states in the conduction band, remaining in these states for a short time. The energy of these electrons decreases rapidly and they return to the valance band, emitting light.

In order to detect the light emitted (which is not visible to the human eye), one has used a photographic camera with parameters adjusted to see the UV range.

In this way, a first experiment was arranged using:

A magnetic induction electronic apparatus capable of working at a frequency ranging from 500 Hz to 2 KHz (in the experiment one worked below 1 KHz). In an embodiment of the present invention, one uses the same specification of magnetic field inductor, but with a few operational improvements, as for instance a protection box. An example of an inductor used is that of the mark M_GAGE® Model Q7MEB of the Banner Engineering company;

An illuminating source of UV with a range of 80-90 nm. In an embodiment of the present invention, one uses LED with an adjustable range from 0 to 379 nm. In an example of illuminator used is the ITSLUXO®, an UV LED illuminator from Pumatronix;

An image capturing device such as a photographic camera, with register of 60 frames per second and shutter speed of $\frac{1}{2000}$ s (frequency adjustable between 40 and 70 Hertz). In this experiment, it was calibrated at 50 Hertz; range adjustable between 0 and 850 nm. In the experiment, it was calibrated for 3 ranges: UV (80-90 nm), visible (380-779 nm), and infrared (780-850 nm). An example of camera used is the ITSCAM® camera from Pumatronix;

an infrared illuminator—300 LEDs (range 850 nm);

A computer provided with a software capable of communicating with the camera, processing and seeing the image. The software is capable of analyzing the pixels that compose each frame and, in this way, identifying any different pattern of organic particles like sugar particles; and Samples of organic particles like pure sugar, and inorganic particles like sand.

Various configurations of sugar plus sand mixtures were tested.

In all the cases the difference in photoluminescence between the two materials could be identified by the camera and registered by the system connected to it.

On the basis of the results of the above test, the objectives for the embodiment of the invention were delimited so as to make the solution viable for use in the field. For this purpose, one considered that:

1—The solution should be capable of operating continuously in the hopper discharge flow. In order to define the best point (s), it would be necessary to determine the maximum thickness in which it is possible to detect precisely the presence of contaminants;

2—The solution should also be capable of monitoring the exit of the product from the warehouse to the ship, since it would be a second barrier between the product going to the ship of the client. Although it is not possible to identify the agent causing the contamination at this moment, this would prevent greater commercial damage. Besides, some trucks are unloaded directly at the warehouses, without passing though hoppers. In other words, it would be necessary to present a solution with portability; and 3—A software for automatic detection and warning about contaminants above 500 ppm should be developed.

Other detection alternatives were studied:

A portable detection apparatus: for analysis of samples at point that will not have the solution installed, for instance, unloading directly at warehouses (without going through hoppers); and A solution capable of detecting the differences between the different loads of organic particles received by the importing/exporting company, like sugar VI, V2 and V3, so as to prevent a product A from being unloaded at a hopper operating with product B.

DETAILED DESCRIPTION OF THE INVENTION

The objective of the present invention is to generate and report the degree of purity of the load of particulate organic material, such as sugar, by sampling, capturing and evaluating images rigorously within the process.

The images are captured by cameras that generate consecutive static images of the product being rolled by the pieces of equipment for storage and/or transportation.

The images are saved in named filed, the ways of which are stored in a databank (Oracle or SQL) by software constituted by there applications:

sensible access, for viewing images and generating alarms;

sensible administrator, for configuring parameters and pieces of equipment; and sensible service, which is a background service that effectively monitors the whole system.

This software, produced in C++, java, java flex language, evaluates the images according to an algorithm especially developed for this purpose. This evaluation follows parameters configured through the software in the same databank. One also keeps the results of the evaluations of the degree of purity of the particulate organic material (for example, sugar), alarms, and records of alarms are generated for the acceptable level of impurity, also in conformity with the pre-configured parameters for the particulate organic material to be analyzed.

The Algorithm

The image captured is transformed into bitmap of pixels of color components RGB (Red, Green, Blue), discretized in integer values ranging from 0 (zero) to Cmax (where Cmax is higher than or equal to 16). A 0 (zero) color component indicates that no color intensity was detected and Cmax indicates that the maximum value was detected. Intermediate values are provided to the color component for that pixel.

The camera should supply the images with tonalities adjustable for the called color, accepted color, which corresponds to the product considered to be good, where the product is the particulate organic material. The accepted color is defined within the parameters determined.

One chooses a primary color component called "B" as the accepted color. Other tonalities are considered non-accepted according to the parameters: saturation rigor and hue tolerance.

The software code in C++, herein called isAcceptedColor, for indicating that the color pixel described above is of accepted color "B" is given by:
Bool isAcceptedColor=(b>(r+s))
&& (b>(g+s)O
77 (abs(r−g)<=m);

"R" and "G" are called other primary colors than the primary color "B" of components "r" and "g". The parameter s, called saturation rigor, should be smaller than Cmax, and the greater it is the more rigorous the determination of the primary color "B" will be with regard to saturation, that is, more colorful than grayish. And the parameter m, called hue tolerance, has actuation as parameter if it is smaller than (Cmax−s), and the greater it is the more tolerant it will be in the characterization of the primary color "B" with respect to the hue, that is, less centered on the primary color "B" than on the other primary colors "R" and "G".

The parameters s and m are adjusted so as the portion of pixels of the accepted color will coincide with the accepted material in the image, while the impurities give a false result for the calculation of the isAcceptedColor code using the same parameters s and m for the same conditions (same camera, same illumination, same settings of the camera).

A proportion of number of pixels of accepted color with the total of pixels of the image area is made.

The invention will be described hereinafter with reference to the figures.

Figure 1:
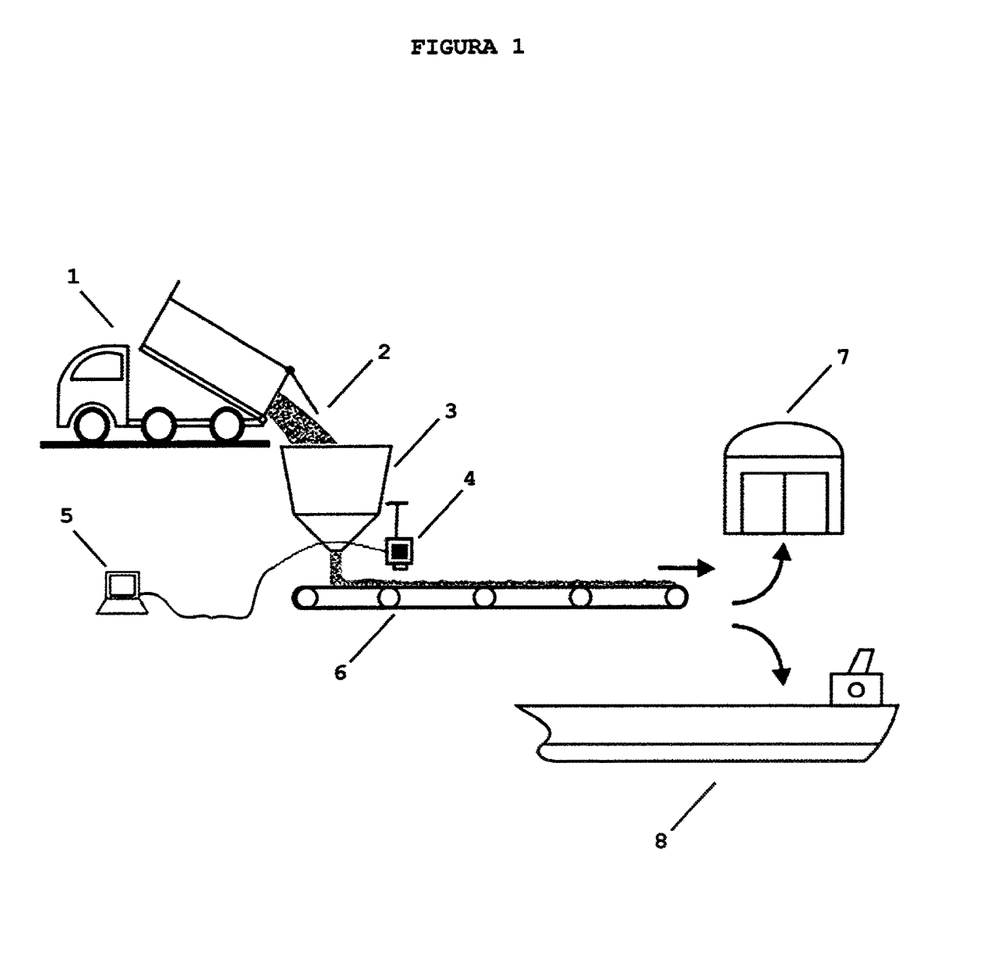
FIG. 1 illustrates the diagram of the process of the present invention, where one exemplifies the application of the present invention at the moment of unloading a truck of sugar at a hopper that discharges onto a conveyer-belt that can carry the sugar to a warehouse or directly to a ship for exportation.

As shown in FIG. 1, an example of application of the process of the present invention, a truck (1) discharges the load (2) of an organic particulate material into a hopper.

The load falls out of the hopper onto a conveyor-belt (6), which leads the material to a warehouse (7) or directly to a ship (8) for exportation or to a freight train, if the load is to be transported to another point.

Figure 2:
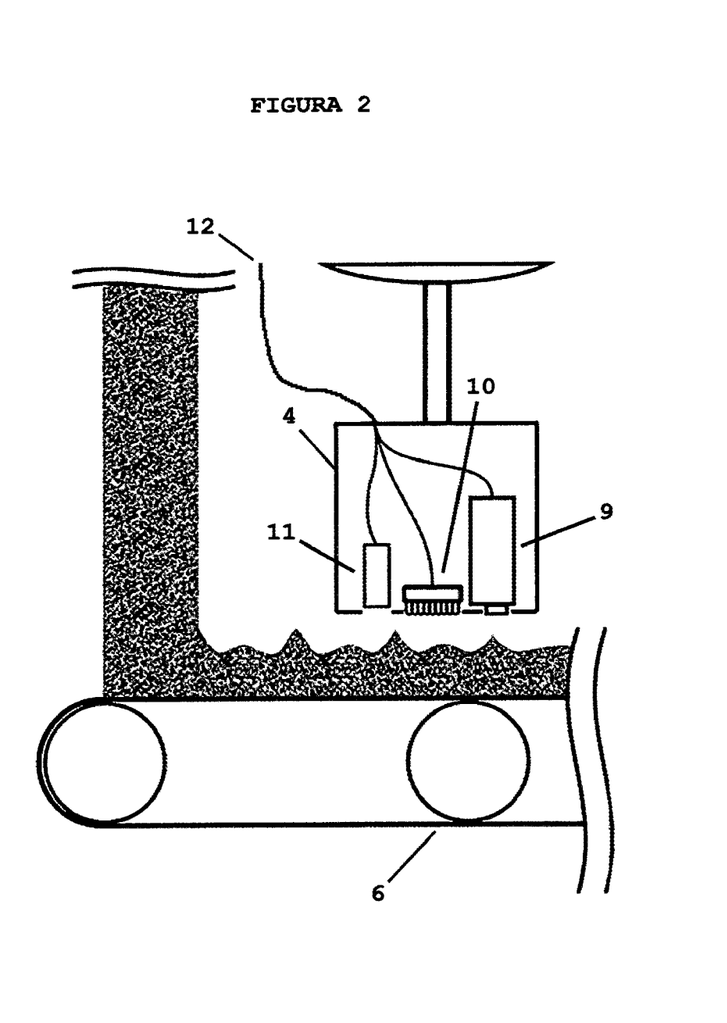
FIG. 2 illustrates, in a diagram, the device of the present invention.
Figure 3:
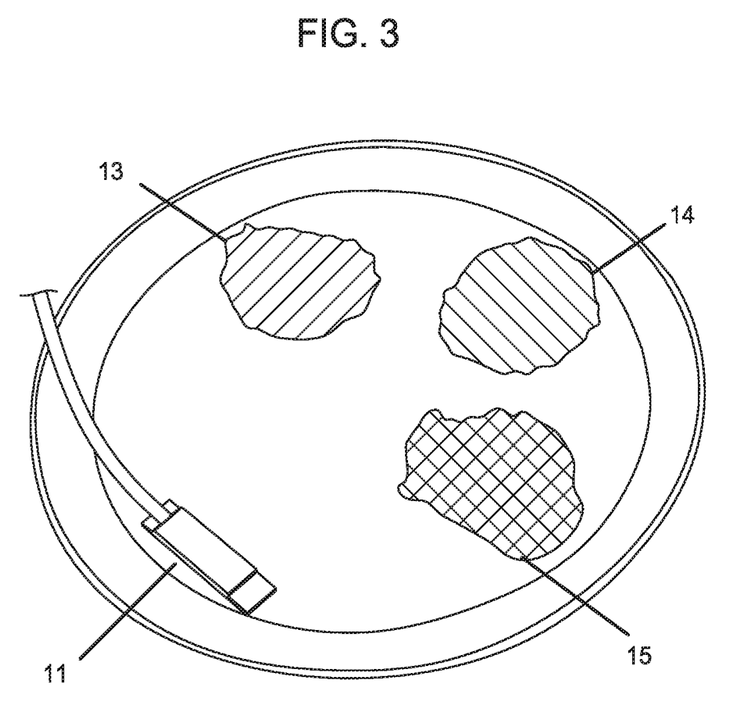
FIG. 3 shows a sample of the particulate organic material, in this case sugar (13), and the particulate inorganic material, in this case sand (14), and the mixture of the two materials (15) so as to enable verification that it is not possible to the human eye to tell whether load of sugar is contaminated with sand or not.
Figure 4:
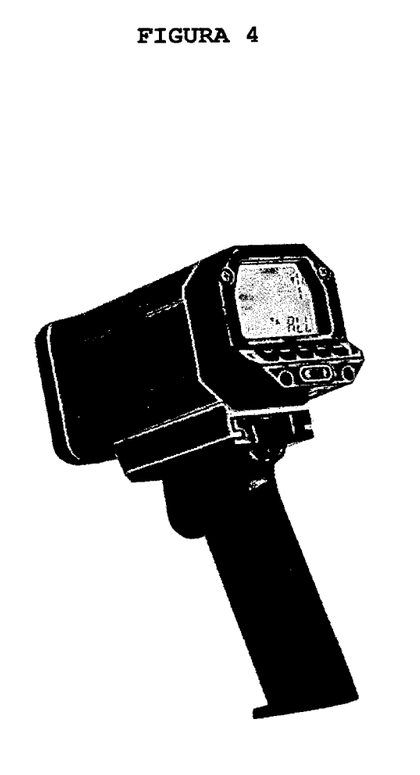
FIG. 4 illustrates a model of the portable device of the present invention.

Between the exit from the hopper (3) and the conveyor-belt (6) one positions a source of magnetic field, at least one source of illumination, at least one photographic camera, and a computer, as shown in FIG. 2.

The source of magnetic field (11) of the device (4) emits a field with frequency ranging from 500 to 2 Khz, preferably with frequency ranging from 800 Hz to 1.2 KHz, and more preferably emits a field with frequency of 1.0 KHz.

The source of illumination (10) of the device (4) emits light in the range from 0 to 850 nm. The source may emit an ultraviolet source in the range of 0-379 nm. The source of illumination (10) may be a UV LED one and emit ultraviolet in the range 80-90 nm, or the source of illumination (10) may be a source of infrared LEDs and emit a 850 nm.

The photographic camera (9) of the device (4) enables setting to register at least 60 frames per second, with shutter speed of at least ½000 s with frequency between 40 and 70 Hz, and calibration of three ranges of light, ultraviolet from 80 to 90 nm, visible from 380 to 779 and infrared from 780 to 850 nm.

The source of magnetic field (11), the source of illumination (10) and the camera (9) of the device (4) are connected to a computer (5) which may be encapsulated together with the other elements of the device or may be arranged separately, depending on the configuration and application of the device.

In applications at unloading places, since the sampling takes place in a dynamic manner, that is, the load of particulate material is in constant movement between the exit of the hopper (3) and the conveyor-belt (6), and in order that it can cover a larger surface area of the blade formed by the falling organic particulate material at the hopper (3) outlet, more cameras (9), sources of illumination (10) and sources of magnetic field (11) may be installed on the device (4), increasing the capacity of monitoring the material.

Figure 5:
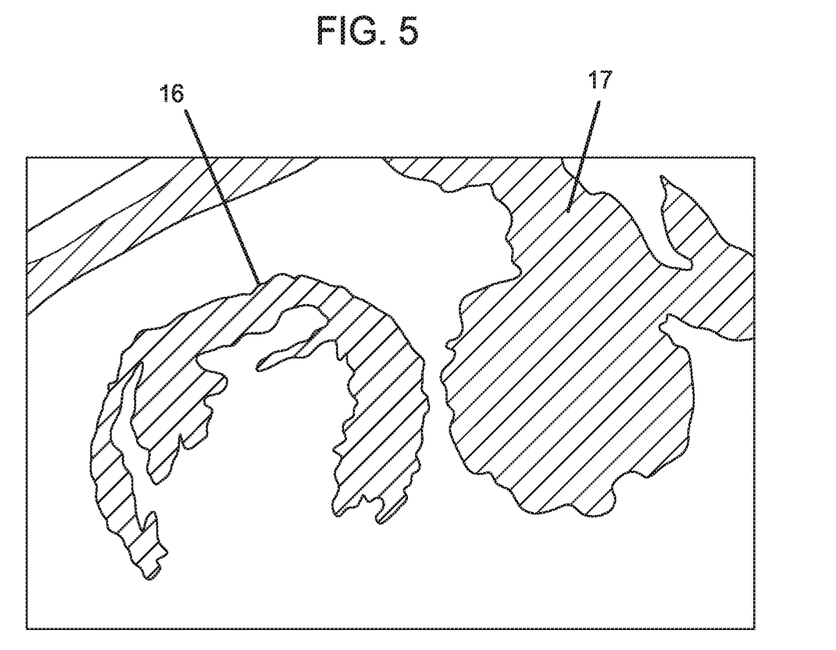
FIG. 5 illustrates the photograph made by the device of the present invention of a small sample of organic particulate material (16) and a small sample of inorganic particulate material (17).
Figure 6:
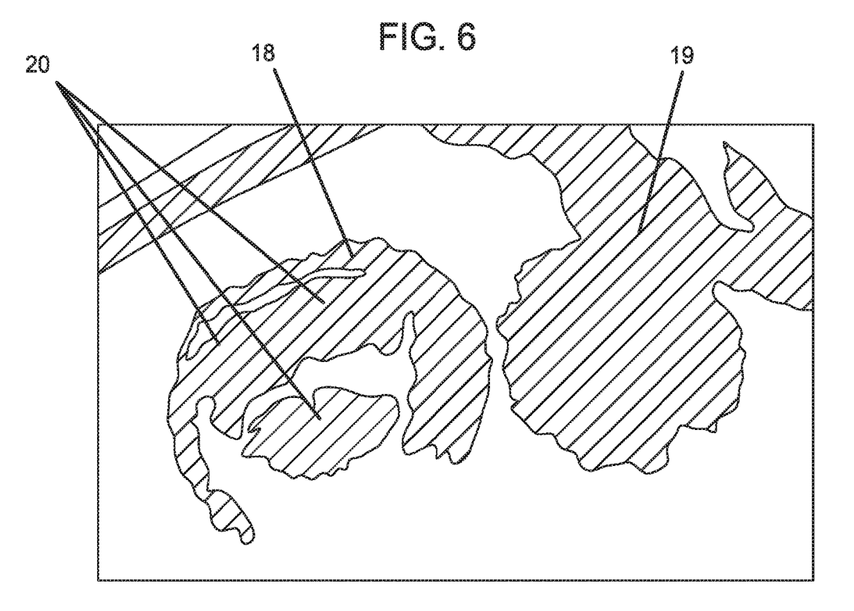
FIG. 6 illustrates the photograph made by the device of the present invention of a small sample of organic particulate material (18) contaminated with portions of inorganic particulate material (20) and a small sample of inorganic particulate material (19).
Figure 7:
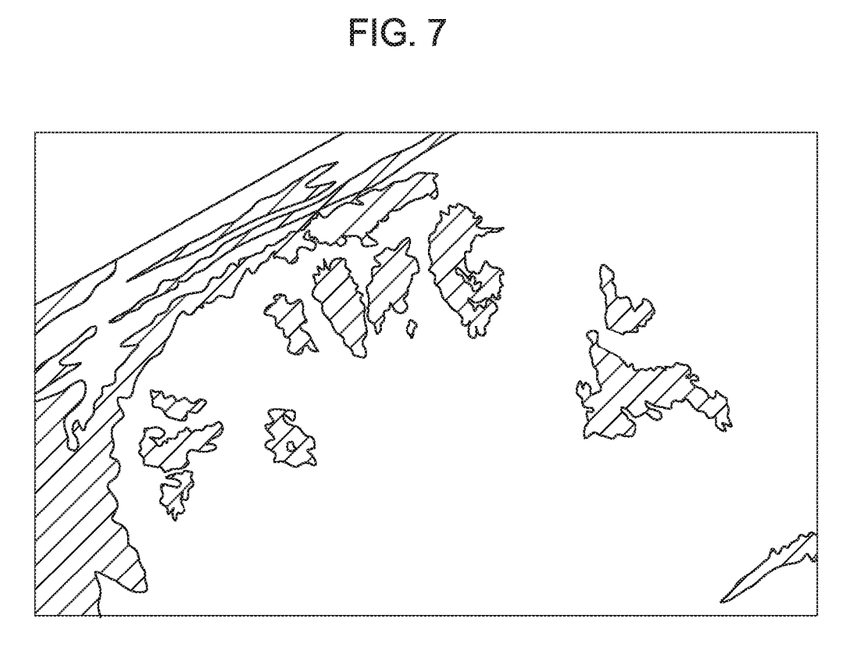
FIG. 7 illustrates the photograph made by the device of the present invention of a mixture of organic particular material with inorganic particulate material, demonstrating the detection of contamination of the organic material, of darker color, by the inorganic material, of clearer color, so that the image analyzing software can tell the presence or absence of contaminants and whether this contamination is within the internationally acceptable parameters or not.

The process for identifying inorganic particles that contaminate loads containing organic particles, as shown in FIG. 1, is characterized by having the steps of:
(a) a sample of the load of organic particles is collected in a dynamic or static manner; in the dynamic form the load is discharged from a truck (1), or from any other means of transporting loads such as a train or a ship, into a hopper (3) which tapers the load and discharges it onto a conveyer-belt (6);
(b) the device (4) located between the hopper (3) and the conveyor-belt (6) magnetizes the sample of organic particulate material that falls out of the hopper with at least one magnetic field at frequency between 500 Hz and 2 KHz, preferably between 800 Hz and 1.2 KHz, and more preferably at the frequency of 1.0 KHz;
(c) the device (4) illuminates the sample with at least one source of illumination in the range from 0 to 850 nm. The source of illumination may emit ultraviolet in the range from 0 to 379 nm, the source of illumination may be a source of UV LED and emit ultraviolet in the range from 80 to 90 nm, or the source of illumination may be infrared LEDs and emit 850 nm;
(d) the device (4) captures images of the sample with at least one photographic camera set to register at least 60 frames per second, with shutter speed of at least ½000 s with frequency between 40 and 70 Hz, and calibration of three ranges: ultraviolet from 80 to 90 nm; visible from 380 to 779 and infrared from 780 to 850 nm;

The images are sent to the computer for processing, evaluation and judgement of the image. FIGS. 5 to 7 illustrate the images generated by the device and analyzed by the software. FIG. 5 shows that the organic particulate material (16) does not emit light and the inorganic particulate material (17) emits strong light. FIG. 6 shows that the contamination of the sample of organic particulate material (18), per portions of inorganic particulate material (20), is easily identified by the software of the present device (4). FIG. 7 shows how a mixture of organic particulate material with inorganic particulate material is monitored by the device (4) and the detection of the contamination of the organic material is made, and the darker color represents the organic material, and the clearer color represents the inorganic material. In this way, the software for analysis of images can make the judgment of the presence or absence of contaminants and whether the contamination is within the internationally acceptable parameters or not, according to the above-described algorithm,
(e) the software of the device diagnoses the sample as being either contaminated or not, on the basis of the parameter of 500 ppm as being the accepted limit of contaminants in the load, and, after the diagnose,
(f) the device gives command to block or release the load to be stored at a warehouse (7) or in a ship (8) for exportation.

The steps of magnetization, illumination and capture of images are managed so as to obtain the images with quality sufficient to make the contamination diagnose.

The invention claimed is:
1. A process for identifying inorganic particles that contaminate loads containing organic particles, comprising:

collecting a sample of the load of organic particles, in a dynamic or static manner;

magnetizing the sample with at least one magnetic field with frequency between 500 Hz and 2 KHz;

illuminating the sample with at least one source of illumination in the range from 0 to 850 nm;

capturing images of the sample with at least one photographic camera configured to register at least 60 frames per second, with shutter speed of at least 1/2000 of a second, with frequency between 40 and 70 HZ, and calibration of three ranges: ultraviolet from 80 to 90 nm; visible from 380 to 779 nm, and infrared from 780 to 850 nm;

sending the images to the computer for processing, evaluation and judgment of the image;

diagnosing the sample as being contaminated or not;

blocking or releasing the load.

2. The process according to claim 1, wherein the source of magnetization works at the frequency between 800 Hz and 1.2 KHz.

3. The process according to claim 1, wherein the magnetizing source works at the frequency of 1.0 KHz.

4. The process according to claim 1, wherein the source of illumination emits ultraviolet in the range from 0 to 379 nm.

5. The process according to claim 1, wherein the source of UV LED illumination emits ultraviolet in the range from 80 to 90 nm.

6. The process according to claim 1, wherein the source of infrared LEDs illumination emits 850 nm.

7. A device for identifying inorganic particles that contaminate loads containing organic particles, having at least one source of magnetic field, at least one source of illumination, at least one photographic camera, and a computer.

8. The device according to claim 7, wherein the source of magnetic field emits a field with frequency between 500 Hz and 2 Khz.

9. The device according to claim 7, wherein the source of magnetic field emits a field with frequency between 800 Hz and 1.2 KHz.

10. The device according to claim 7, wherein the source of magnetic field emits a field with frequency of 1.0 KHz.

11. The device according to claim 7, wherein the source of illumination emits light in the range from 0 to 850 nm.

12. The device according to claim 7, wherein the source of illumination emits ultraviolet in the range from 0 to 379 nm.

13. The device according to claim 7, wherein the source of illumination is a UV LED source of illumination and emits ultraviolet in the range from 80 to 90 nm.

14. The device according to claim 7, wherein the source of illumination is a source of infrared LEDs illumination and emits 850 nm.

15. The device according to claim 7, wherein the photographic camera enables setting to register at least 60 frames per second, with shutter speed of at least 1/2000 of a second, with frequency between 40 and 70 Hz, and calibration of three ranges: ultraviolet from 80 to 90 nm; visible from 380 to 779 nm, and infrared from 780 to 850 nm.

* * * * *